United States Patent [19]

Falkowski et al.

[11] Patent Number: 4,783,527

[45] Date of Patent: Nov. 8, 1988

[54] AMIDES OF AMPHOTERIC POLYENE MACROLIDE ANTIBIOTICS

[75] Inventors: Leonard S. Falkowski; Andrzej B. Jarzebski, both of Gda sk; Barbara J. Stefa ska; Elzbieta Troka, both of Gda sk-Oliwa; Edward Borowski, Gdansk-Wrzeszcz, all of Poland

[73] Assignee: Politechnika Gdanska, Poland

[21] Appl. No.: 276,462

[22] Filed: Jun. 23, 1981

Related U.S. Application Data

[63] Continuation of Ser. No. 138,356, Apr. 8, 1980, abandoned.

[30] Foreign Application Priority Data

Apr. 9, 1979 [PL] Poland .................................. 214802

[51] Int. Cl.⁴ ............................................ C07H 17/08
[52] U.S. Cl. ...................................... 536/53; 536/6.5; 514/31
[58] Field of Search ................... 536/6.5, 53

[56] References Cited

U.S. PATENT DOCUMENTS 4,035,568 7/1977 Schaffner et al. ................. 536/6.5
4,041,232 8/1977 Sipos et al. ......................... 536/6.5

OTHER PUBLICATIONS

Noller, "Chemistry of Organic Compounds", W. B. Saunders Co., Phila., Pa., 1965, pp. 186 and 529.

*Primary Examiner*—Ronald W. Griffin
*Assistant Examiner*—Nancy S. Carson

[57] ABSTRACT

The invention relates to amides of polyene macrolide antibiotics and their derivatives characterized by the general formula I,

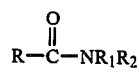

where R is the polyene macrolide, $R_1$ is an alkyl or isoalkyl chain of from one to eighteen carbons, unsubstituted or substituted with a primary or secondary amine; where $R_2$ is an hydrogen or $R_1$ or $R_1$ and $R_2$ are joined through the nitrogen to form a heterocyclic ring.

The method of preparation of these substances according to our invention depends upon the reaction of the polyene macrolide or its derivative in which the carboxylic group is activated; in the environment of an organic solvent or mixture of solvents and in the presence of a substance neutralizing the acid; with a compound containing an amino group; leaving upon completion of the reaction, and precipitation of the product from the reaction mixture, by addition of ethyl ether or a mixture of ethyl ether with hydrocarbons; isolation and purification of the product by means of known methods.

11 Claims, 1 Drawing Sheet

U.S. Patent      Nov. 8, 1988      4,783,527
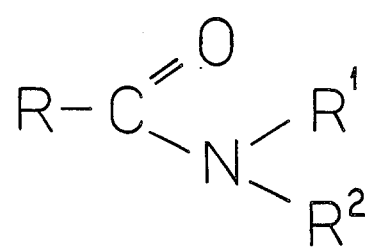

AMIDES OF AMPHOTERIC POLYENE MACROLIDE ANTIBIOTICS

This is a continuation, of application Ser. No. 138,356, filed Apr. 8, 1980, abandoned.

The invention relates to amides of polyene macrolide antibiotics and their derivatives characterized by the general formula I

where R is the residue of the polyene carboxylic macrolide, RCOOH. $R_1$ is an alkyl or isoalkyl chain of from one to eighteen carbons unsubstituted or substituted with a primary or secondary amine; and $R_2$ is an hydrogen, or $R_1$; or $R_1$ and $R_2$ are joined through the nitrogen to form a heterocyclic ring.

BACKGROUND OF THE INVENTION

Known are derivatives of polyene macrolide antibiotics such as the complex of amphotericin B with sodium deoxycholate named Fungizone, N-acyl, N-glycosyl and alkyl esters.

THE INVENTION

Amides of polyene carboxylic macrolide antibiotics and their derivatives and the method of their preparation have not been know. This invention relates to amides of polyene carbocyclic macrolide antibiotics and their derivatives characterized by the general formula I

where R is the residue of the polyene carboxylic macrolide RCOOH and $R_1$ is an alkyl or isoalkyl chain of from one to eighteen carbons, unsubstituted or substituted with primary or secondary amine or aralkyl; and $R_2$ is hydrogen, or $R_1$; or $R_1$ and $R_2$ are joined through the nitrogen to form a heterocyclic ring.

The method of preparation of these antibiotic substances, comprising amides of polyene macrolides and their derivatives, characterized by the general formula I, where R, $R_1$ and $R_2$ have the above indicated meanings, according to our invention; is based upon the reaction of the polyene macrolide or its derivative, in which the carboxylic group is activated in the presence of an organic solvent or mixture of such solvents and in the presence of a substance for neutralizing the acid, with a compound containing an amino group; maintaining the reactants until completion of the reaction and then precipitating the product from the reaction mixture by the addition of ethyl ether or mixtures of ethyl ether with hydrocarbons followed by isolation and purification of the product by known methods.

DETAILED DESCRIPTION

The polyene macrolide antibiotics for this invention are those which contain in their molecule a free carboxylic group, such as: amphotericinB, pimaricin, nystatin, polyfungin, aureofacin, candicidin, and levorin.

As derivatives of polyene macrolide antibiotics applied where those substances, in which the aliphatic amino group of the base residue was substituted with N,N-dimethylaminomethyl, 3-carboalkoxy-propanyl-2, 4-oxo=pentanyl-2, glycosyl and acyl.

The substances which activate the carboxylic group of these polyene macrolides are diphenyl phosphorazidate (DPPA) and N-hydroxybenzotriazote (HBT) with dicyclohexylcarbodiimide (DCC).

The organic solvents were N,N-dimethylformamide, (N,N-dimethylacetamide; dimethylsulphoxide; aliphatic alcohols with chain length of from one to five carbons; or mixtures thereof.

Substances used for neutralizing the acid liberated were triethylamine and N-methyl-morpholine.

The method of preparing the polyene macrolide amides of this invention enables substitution of the carboxylic group on the base residue without affecting the remaining part of the antibiotic molecule. This is demonstrated by means of spectroscopic methods. The complete structural analysis indicates amphotericin B n-hexyl amide. The electronic absorption spectra of that derivative and the parent antibiotic were identical, which indicated an unchanged chromophore portion of the molecule. The extinction coefficient: $E_{1\ cm}^{1\%} = 1320$ at $=382$ nm showed the high purity of the obtained substance. In the infrared spectrum, characteristic was the lack of bands at 1560 and 1695 cm$^{-1}$ assumed in amphotericin B as symmetric asymmetric stretching vibrations of the carboxylic group and the presence of bands at 1640 cm$^{-1}$ typical for the carbonyl function of secondary amides. That provides direct evidence of the amide bond in the synthesized compound. The field desorption mass spectrum of amphotericin-B-n-hexylaminde; N-acetylamphotericin-B-n-hexylamide; and N-acetyl-methoximino-amphotericin-B-n-hexylamide was at m/z 1006, 1048 and 1091 respectively. The electronic impact mass spectrum of N-acetyl-methoximino-per-o-trimethylsilylamphotericin-B-n-hexylamide; and N-acetyl-methoximinoper-o-trimethylsilyl-perhydroamphotericin-B-n-hexylamide revealed molecular ions at m/z 1768 and 1811 respectively. These values strictly correspond to the molecular weights of the derivatives, whereas the observed fragmentation ions agree with the known fragmentation rules. This provides positive evidence for the postulated structure of the compounds of the invention.

All the synthesized compounds of this invention as shown in the Examples had been characterized by means of electronic and infrared absorption spectra and field desorption mass spectra. The above described method had been applied in syntheses of polyene macrolide amides and their derivatives in which the substituents displayed different lipophility and contained various functional groups, such as hydroxy, carbomethoxy, substituted amino. Substances which contained a dimethylamino group readily formed water soluble salts.

N-substituted polyene macrolides formed the appropriate amides under more convenient conditions as compared with antibiotics containing the free amino group. Amides of polyene macrolides in which the amino group salts of the saccharide moiety was substituted with N,N-dimethyl methin, 4-oxo-pentenyl-2 or 5-carboethoxy propenyl-2 could be transformed into compounds with free aliphatic amino group using our previously described methods.

The advantages of the amide derivatives of polyene macrolide antibiotics described in our invention are their higher antifungal activities together with improved in-vitro selective toxicities as compared with the parent antibiotics. Additionally the polyene macrolide amides form water soluble salts. The amides of polyene macrolide antibiotics and their derivatives and the method of their mode of preparation according to this invention are presented by the following examples:

EXAMPLE I 462 mg of amphotericin B ($E_{1\ cm}^1 = 1420$ at 382 nm) was suspended in 10 ml of N,N-dimethylacetamide (DMA) and 10 ml of methanol (MeOH) and treated in sequence with 0.62 ml of n-hexylamine, 1.02 ml of diphenyl phosphoracidate (DPPA) and 0.69 ml of triethylamine (TEA). The reaction mixture was stirred 4 hours at room temperature and subsequently the crude product precipitated with ethyl ether:petroleum ether 1:1 mixture.

The precipitate was dissolved in butanol, the solution washed two times with water and concentrated under vacuum up to complete removal of the water. The amphotericin B n-hexylamide was precipitated with ethyl ether, washed with this solvent and dried in vacuum.

The product was purified by means of chromatography on silica gel saturated with water using as solvent system chloroform:methanol:water at 50:10:1. 265 mg of amphotericin B n-hexyl amide was obtained (55% of the theoretical yield), which exhibited $E_{1\ cm}^{1\%} = 1670$ at 382 nm and $IC_{50} = 0.1$ mcg/ml.

EXAMPLE II 66.5 mg of pimaricin ($E_{1\ cm}^1 = 980$ at 304 nm) was dissolved in 10 ml of dimethylsulphoxide (DMSO) and treated in sequence with 0.09 ml of morpholine, 0.21 ml DPPA and 0.14 ml TEA. The reaction was conducted 4 hours at 36° C. and further worked up as described in Example 1. 29 mg of pimaricin morpholine amide was obtained (40% of the theoretical yield), which exhibited $E_{1\ cm}^1 = 800$ at 304 nm and $IC_{50} = 3.1$ mcg/ml.

EXAMPLE III 66.5 mg of pimaricin ($E_{1\ cm}^1 = 980$ at 304 nm) was dissolved in 2 ml of N,N-dimethylformamide (DMF) and treated in sequence with 0.11 ml of benzylamine, 0.21 ml DPPA and 0.14 ml TEA and further worked up as described in example 2. 35 mg of pimaricin benzylamide was obtained (47% of the theoretical yield) which exhibited $E_{1\ cm}^{1\%} = 804$ at 304 nm and $IC_{50} = 0.8$ mcg/ml.

EXAMPLE IV 300 mg of pimaricin ($E_{1\ cm}^1 = 980$ at 304 nm) was dissolved in 15 ml of DMA and treated in sequence with 0.15 ml of n-butyl amine, 0.4 ml DPPA and 0.3 ml TEA. The reaction was allowed to proceed for 15 hours at room temperature and the crude product precipitated with ethyl ether-petroleum ether 2:1 mixture. The precipitate was dissolved in butanol, the solution washed two times with water and concentrated under vacuum up to complete removal of the water. The product was precipitated with ethyl ether, washed with this solvent and dried in vacuum. 500 mg of pimaricin n-butyl amide was obtained (77% of the theoretical yield) which exhibited $E_{1\ cm}^{1\%} = 700$ at 304 nm and $IC_{50} = 1.5$ mcg/ml.

EXAMPLE V 500 mg of N-glycosylpolyfungin ($E_{1\ cm}^{1\%} = 480$ at 304 nm) was dissolved in 2 ml of DMA and treated in sequence with 0.11 ml of n-butyl amine, 0.6 ml DPPA and 0.4 ml TEA.

The reaction was conducted 6 hours at room temperature and further washed up as described in Example I. 305 mg of N-glycosylpolyfungin n-butyl amide was obtained (50% of the theoretical yield) which exhibited $E_{1\ cm\%}^1 = 400$ at 304 nm and $IC_{50} = 0.8$ mcg/ml.

EXAMPLE VI 200 mg of aureofacin ($E_{1\ cm}^{1\%} = 600$ at 382 nm) was suspended in 4 ml of DMA and treated in sequence with 0.32 ml of n-butylamine, 0.25 ml DPPA and 0.38 ml TEA. the reaction mixture was stirred 4 hours at room temperature and further worked up as described in Example I. 120 ml of aureofacin n-butyl amide was obtained (56% of the theoretical yield) which exhibited $E_{1\ cm}^{1\%} = 730$ at 382 nm and $IC_{50} = 0.003$ mcg/ml.

EXAMPLE VII 100 mg of polyfungin ($E_{cm}^{1\%} = 704$ at 304 nm) was dissolved in 10 ml of DMA and treated in sequence with 0.75 ml of 3-(N,N-dimethylamine)propylamine, 1 ml DPPA and 0.7 ml TEA. The reaction proceeded for 12 hours at room temperature and was further worked up as described in Example IV. 130 mg of polyfungin 2-hydroxyethylamide (76% of theoretical yield) which exhibited $E_{1\ cm}^{1\%} = 500$ at 304 nm and $IC_{50} = 0.5$ mcg/ml.

EXAMPLE VIII 450 mg of polyfungin ($E_{cm}^{1\%} = 600$ at 304 nm) was dissolved in 10 ml of DMA and treated in sequence with 0.75 ml of 3-(N,N-dimethylamine)propylamine, 1 ml DPPA and 0.7 ml TEA. The reaction proceeded for 3 hours at room temperature and subsequently the crude product was precipitated with ethyl ether:petroleum ether 1:2 mixture. The precipitate was dissolved in butanol, the solution washed two times with water and concentrated under vacuum up to complete removal of the water.

The polyfungin 3-(N,N-dimethylamino)propylamide of polyfungin was precipitated with ethyl ether, washed with this solvent and dried in vacuum. The crude derivative was purified by means of chromatography on Sephadex (Trade Mark) LH-20 saturated with water using as solvent system chloroform:methanol:water (20:10:1 v/v). 250 mg of polyfungin 3-(N,N-dimethylamino)propylamide was obtained (51% of the theoretical yield) which exhibited $E_{1\ cm}^{1\%} = 560$ and $IC_{50} = 0.13$ mcg/ml.

EXAMPLE IX 450 mg of polyfungin ($E_{cm}^{1\%} = 600$ at 304 nm) was dissolved in 10 ml of DMA—DMS 1:1 and treated in sequence with 80 mg of 3-(N-isopropylamino)propylamine dihydrochloride, 1 ml DPPA and 0.7 ml TEA. The reaction mixture was stirred 4 hours at room temperature the undissolved amine hydrochloride centrifuged and further worked up as described in Example IV. 350 mg of polyfungin 3-(N-isopropylamino)-propylamide was obtained (71% of the theoretical yield) which exhibited $E_{cm}^{1\%} = 440$ at 304 nm and $IC_{50} = 0.6$ mcg/ml.

EXAMPLE X 450 mg of polyfungin ($E_{cm}^{1\%} = 600$ at 304 nm) was dissolved in 10 ml of DMA—MeOH 4:1 and treated in sequence with 0.75 mg of 1-(N,N-dimethylamino)-2- propylamine, 1 ml DPPA and 0.7 ml TEA. The reaction proceeded for 6 hours at 15° C. and was further worked up as described in Example IV. 307 mg of polyfungin 10(N,N-dimethylamino)isopropyl amide was obtained (77% of the theoretical yield) which exhibited $E_{cm}^{1\%}=408$ at 304 nm and $IC_{50}=0.12$ mcg/ml.

EXAMPLE XI 923 mg of amphotericin B ($E_{cm}^{1\%}=1420$ at 382 nm) was suspended in 30 ml DMA and treated in sequence with 1.57 ml of n-dodecylamine, 2.04 DPPA and 1.38 TEA. The reaction mixture was stirred 5 hours at room temperature and the crude product precipitated with ethyl ether—petroleum ether 1:1. It was further purified by means of counter-current distribution using as solvent system chloroform—methanol—water 2:2:1. 280 mg amphotericin B n-dodecylamide was obtained (26% of the theoretical yield) which exhibited $E_{cm}^{1\%}=1160$ at 382 nm and $IC_{50}=1.1$ mcg/ml.

EXAMPLE XII 923 mg of amphotericin B ($E_{cm}^{1\%}=1420$ at 382 nm) was suspended in 30 ml DPPA—MeOH 2:1 and treated in sequence with 1 ml of isobutyl amine, 2.04 DPPA and 1.38 TEA. The reaction mixture was stirred 4 hours at room temperature and further worked up as described in Example XI. 300 mg was obtained of amphotericin B isobutylamide (31% of the theoretical yield) which exhibited $E_{cm}^{1\%}=1420$ at 382 nm and $IC_{50}=0.59$ mcg/ml.

EXAMPLE XIII 923 mg of amphotericin B ($E_{cm}^{1\%}=1420$ at 382 nm) was suspended in 25 ml DMA and treated in sequence with 1.21 ml of cyclohexylamine, 2.04 DPPA and 1.38 TEA. The reaction mixture was stirred 5 hours at 20° C. and further worked up as described in Example XI. 270 mg was obtained of amphotericin B cyclohexylamide (27% of the theoretical yield) which exhibited $E_{cm}^{1\%}=1350$ at 382 nm and $IC_{50}=0.095$ mcg/ml.

EXAMPLE XIV 923 mg of amphotericin B ($E_{cm}^{1\%}=1420$ at 382 nm) was suspended in 20 ml DMA and treated in sequence with 0.86 ml of isopropylamine, 2.04 DPPA and 1.38 TEA. The reaction mixture was stirred 5 hours at room temperature and further worked up as described in Example XI. 370 mg was obtained of amphotericin B isopropylamide (38% of the theoretical yield) which exhibited $E_{cm}^{1\%}=130$ at 382 nm and $IC_{50}=0.097$ mcg/ml.

EXAMPLE XV 923 mg of amphotericin B ($E_{cm}^{1\%}=1420$ at 382 nm) was suspended in 29 ml DMA and treated in sequence with 2.69 g of n-octadecylamine, 2.04 DPPA and 1.38 ml of TEA. The reaction mixture was stirred 5 hours at room temperature, the undissolved n-octadecylamine centrifuged and the product further worked up as described in Example XI. 220 mg was obtained of amphotericin B n-octadecylamide (19% of the theoretical yield) which exhibited $E_{cm}^{1\%}=780$ at 382 nm and $IC_{50}=21$ mcg/ml.

EXAMPLE XVI 923 mg of amphotericin B ($E_{cm}^{1\%}=1420$ at 382 nm) was suspended in 20 ml DMA and treated in sequence with 0.77 ml of 3-aminopropanol, 2.04 DPPA and 1.5 ml of N-methylmorpholine. The reaction mixture was stirred 4 hours at 25° C., and further worked up as described in Example XI. 340 mg was obtained of amphotericin B 3-hydroxypropylamine (35% of the theoretical yield) which exhibited $E_{cm}^{1\%}=1400$ at 382 nm and $IC_{50}=0.041$ mcg/ml.

EXAMPLE XVII 923 mg of amphotericin B ($E_{cm}^{1\%}=1420$ at 382 nm) was suspended in 35 ml DMA and treated in sequence with 2 g of diethylester 3-aminopropanophosphonic acid hydrochloride, 2.04 ml DPPA and 3.45 ml of TEA. The reaction mixture was stirred 4 hours at room temperature, the undissolved amine hydrochloride centrifuged and further worked up as described in Example XI. 340 mg was obtained of amphotericin B 3-diethylphosphonylpropylamide (32% of the theoretical yield) which exhibited $E_{cm}^{1\%}=1350$ at 382 nm and $IC_{50}=0.19$ mcg/ml.

EXAMPLE XVIII 923 mg of amphotericin B ($E_{cm}^{1\%}=1420$ at 382 nm) was suspended in 25 ml DMA-DMSO 4:1 mixture and treated in sequence with 1.85 g of n-dodecylamine, 2.04 ml DPPA and 1.38 ml of TEA. The reaction mixture was stirred 5 hours at 20° C., and further worked up as described in Example XI. 230 mg was obtained of amphotericin B n-dodecylamide (21% of the theoretical yield) which exhibited $E_{cm}^{1\%}=1040$ at 382 nm and $IC_{50}=4.0$ mcg/ml.

EXAMPLE XIX 923 mg of amphotericin B ($E_{cm}^{1\%}=1420$ at 382 nm) was suspended in 25 ml DMA and treated in sequence with 1.26 ml of 1.3-diaminopropane, 2.04 ml DPPA and 1.38 ml of TEA. The reaction mixture was stirred 5 hours at room temperature, and further worked up as described in Example XI. 190 mg was obtained of amphotericin B 3-aminopropylamide (21% of the theoretical yield) which exhibited $E_{cm}^{1\%}=980$ at 382 nm and $IC_{50}=0.093$ mcg/ml.

EXAMPLE XX 923 mg of amphotericin B ($E_{cm}^{1\%}=1420$ at 382 nm) was suspended in 25 ml DMA and treated in sequence with 1.535 g of the ethyl ester of 4-aminobutyric acid hydrochloride, 2.04 ml DPPA and 1.38 ml of TEA. The reaction mixture was stirred 5 hours at room temperature, the triethylamine hydrochloride centrifuged off, and the mixture further worked up as described in Example XI. 210 mg was obtained of amphotericin B 3-carbomethoxypropylamide (21% of the theoretical yield) which exhibited $E_{cm}^{1\%}=1100$ at 382 nm and $IC_{50}=0.071$ mcg/ml.

EXAMPLE XXI 923 mg of amphotericin B ($E_{cm}^{1\%}=1420$ at 382 nm) was suspended in 20 ml DMA and treated in sequence with 1.65 ml of n-octylamine, 2.04 ml DPPA and 1.38 ml of TEA. The reaction mixture was stirred 4 hours at room temperature, and further worked up as described in Example XI. 240 mg was obtained of amphotericin B n-octylamide (23% of the theoretical yield) which exhibited $E_{cm}^{1\%}=1140$ at 382 nm and $IC_{50}=0.24$ mcg/ml.

EXAMPLE XXII 923 mg of amphotericin B ($E_{cm}^{1\%}=1420$ at 382 nm) was suspended in 20 ml DMA and treated in sequence with 1 ml of piperidine, 2.04 ml DPPA and 1.38 ml of TEA. The reaction mixture was stirred 4 hours at room temperature, and further worked up as described in Example XI. 250 mg was obtained of amphotericin B piperidylamide (25% of the theoretical yield) which exhibited $E_{cm}^{1\%}=1130$ at 382 nm and $IC_{50}=0.14$ mcg/ml.

EXAMPLE XXIII 923 mg of amphotericin B ($E_{cm}^{1\%}=1420$ at 382 nm) was suspended in 20 ml DMA and treated in sequence with glycine amide, 2.04 ml DPPA and 1.38 ml of TEA. The reaction mixture was stirred 5 hours at room temperature, and further worked up as described in Example XI. 300 mg was obtained of amphotericin B glycine amide (31% of the theoretical yield) which exhibited $E_{cm}^{1\%}=900$ at 382 nm and $IC_{50}=0.06$ mcg/ml.

EXAMPLE XXIV 66.5 mg of pimaricin ($E_{cm}^{1\%}=980$ at 304 nm) was dissolved in 2 ml DMA and treated in sequence with 0.09 ml of aniline, 0.21 ml DPPA and 1.14 ml of TEA. The reaction was carried out for 4 hours at room temperature, and further worked up as described in Example I. 30 mg of pimaricin anilide (41% of the theoretical yield) was obtained which exhibited $E_{cm}^{1\%}=800$ at 304 nm and $IC_{50}=1$ mcg/ml.

EXAMPLE XXV 200 mg of candicin ($E_{cm}^{1\%}=800$ at 378 nm) was suspended in 4 ml DMA and treated in sequence with 0.3 ml of n-butylamine, 0.6 ml DPPA and 0.3 ml of TEA. The reaction mixture was stirred 6 hours at room temperature, and further worked up as described in Example IV. 160 mg of candicin n-butylamide (75% of the theoretical yield) was obtained which exhibited $E_{cm}^{1\%}=600$ at 378 nm and $IC_{50}=0.01$ mcg/ml.

EXAMPLE XXVI 200 mg of levorin ($E_{cm}^{1\%}=800$ at 378 nm) was suspended in 4 ml DMA and treated in sequence with 0.3 ml of n-butylamine, 0.6 ml DPPA and 0.3 ml of TEA. The reaction mixture was stirred 6 hours at room temperature, and further worked up as described in Example IV. 160 mg of candicin n-butylamide (75% of the theoretical yield) was obtained which exhibited $E_{cm}^{1\%}=600$ at 378 nm and $IC_{50}=0.01$ mcg/ml.

EXAMPLE XXVIA 200 mg of levorin ($E_{cm}^{1\%}=800$ at 378 nm) was suspended in 5 ml DMA and treated in sequence with 0.3 ml of n-butylamine, 0.6 g DPPA and 0.3 ml of TEA. The reaction mixture was stirred 5 hours at room temperature, and further worked up as described in Example IV. 150 mg of levorin n-butylamide (70% of the theoretical yield) was obtained which exhibited $E_{cm}^{1\%}=550$ at 378 nm and $IC_{50}=0.015$ mcg/ml.

EXAMPLE XXVII 6.5 g of polyfungin ($E_{cm}^{1\%}=600$ at 304 nm) was dissolved in 120 ml DMA and treated in sequence with 8.75 ml of 3-(N,N-dimethylamino)propylamine, 14 ml DPPA and 9.8 ml of TEA. The reaction was continued 5 hours at room temperature, and further worked up as described in Example XI. The resultant 1.7 g of polyfungin 3-(N,N-dimethylamino)propylamide was suspended in 160 ml of water, then 0.467 g of 0.2-asparaginic acid added and stirred 10 minutes at room temperature. The solution was mixed with 250 ml of butanol and concentrated up to complete removal of the water and the product precipitated with ethyl ether washed with that solvent and dried in vacuum. 2.1 g of polyfungin 3-(N,N-dimethyl)propyl amide asparaginic salt was obtained (25% of the theoretical yield) which exhibited $E_{cm}^{1\%}=480$ at 304 nm and $IC_{50}=0.21$ mcg/ml.

What we claim is:

1. An amide of an amphoteric polyene macrolide of the formula

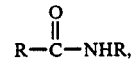

wherein
R is the residue of an amphoteric polyene carboxylic macrolide;
$R_1$ is selected from the group consisting of isopropyl, n-butyl, isobutyl, hexyl, cyclohexyl, n-octyl, n-dodecyl, n-octadecyl, benzyl, phenyl, 2-hydroxyethyl, 3-hydroxypropyl, 3-aminopropyl, 3-carbomethoxypropyl, carbamoylmethyl, 3-(N,N-dimethylamino)-isopropyl, 3-diethylphosphonylpropyl,;
derivatives of said polyene macrolides in which the aliphatic amino groups of the residue is substituted by N,N-dimethylaminomethyl, 3-carboalkoxypropenyl-2, 4-oxopentanyl-2, glycosyl, or acyl;
and the salts thereof.

2. The amide according to claim 1 selected from the group consisting of:
amphotericin B n-hexylamide
pimaricin benzylamide
pimaricin n-butylamide
N-glycosylpolyfungin n-butylamide
aureofacin n-butylamide
polyfungin 2-hydroxyethylamide
polyfungin 3'(N,N-dimethylamino)propylamide
polyfungin 3-(N-isopropylamino)propylamide
polyfungin 1-(N,N-dimethylamino)ispropylamide
amphotericin B n-dodecylamide
amphotericin B isobutylamide
amphotericin B cyclohexylamide
amphotericin B isopropylamide
amphotericin B n-octadecylamide
amphotericin B 3-hydroxypropylamide
amphotericin B 3-diethylphosphonylpropylamide
amphotericin B n-dodecylamide
amphotericin B 3-aminopropylamide
amphotericin B 3-carbomethoxypropylamide
amphotericin B n-octylamide
amphotericin B glycineamide
pimaricin anilide
candicidin n-butylamide
levorin n-butylamide
polyfungin 3-(N,N-dimethyl)propylamide asparginic acid salt.

3. The amides according to claim 1 wherein R is selected from the group of base residues of the amphoteric polyene macrolides having a carboxylic radical, selected from the group consisting of amphotericin B, pimaricin, nystatin, polyfungin, aureofacin, candicidin levorin, N-glycosylpolyfungin.

4. A process for the preparation of the amides of amphoteric polyene macrolide having an activated carboxylic group in the base residue of the formula $$R-\overset{O}{\underset{\|}{C}}-NHR_1$$

wherein
R is the residue of an amphoteric polyenecarboxylic macrolide;
$R_1$ is selected from the group consisting of isopropyl, n-butyl, isobutyl, hexyl, cyclohexyl, n-octyl, n-dodecyl, n-octadecyl, benzyl, phenyl, 2-hydroxyethyl, 3-hydroxypropyl, 3-aminopropyl, 3-carbomethoxypropyl, 3-carbamoylmethyl, 3-(N,N-dimethylamino propyl, 3-(N-isopropylamino)propyl, 1-(N,N-dimethylamino)-isopropyl, 3-diethylphosphonyl propyl;
which comprises the steps of reacting the amphoteric polyene macrolide of the formula:

$$R-COOH$$

with an amine of the formula:

$$H-N-HR_1$$

in a polar organic solvent environment including proton-accepting and carboxy-activating compounds; precipitating the amide by the addition of a non-polar precipitating solvent; and then purifying the amide.

5. The process according to claim 4 wherein the amphoteric polyene macrolide of the formula:

$$R-COOH$$

is selected from the group consisting of amphotericin B, pimaricin, nystatin, polyfungin, aureofacin, candicidin, levorin, N-glycosylpolyfungin and (N,N-dimethyl-)aminomethin amphotericin B and N-acetyl amphotericin B.

6. The process according to claim 4 wherein the amine of the formula:

$$H-NR_1R_2$$

is selected from amines where $R_1$ and $R_2$ are as set forth.

7. The process according to claim 6 where the amine is selected from the group of amines consisting of: hexylamine; morpholine; benzlamine; n-butylamine; ethanolamine; 3-(N,N-dimethylamino) propylamine; 3-(isopropylamino)propylamine; 1-(N,N-dimethylamino)-2-propylamine; n-dodecylamine; isobutylamine; cyclohexylamine; isopropylamine; octadecylamine; propanolamine; aminopropanophosphoric acid. hydrochloride; 1,3-diaminopropane; aminobutyric acid.HCl; octylamine; piperidine; glycinamide; analine.

8. The process according to claim 9, where the polar organic solvent environment is selected from the group consisting of N,N-dimethylacetamide, dimethylsulfoxide, N,N-dimethylformamide, and $C_1$ to $C_5$ alkanols and mixtures thereof.

9. The process according to claim 4 wherein the carboxy-activating compounds are selected from the group consisting of diphenylphosphorazidate, N-hydroxybenzotriazole, dicyclohexylcarbodiimide and mixtures thereof.

10. The process according to claim 4 wherein the proton accepting compounds are selected from the group consisting of trimethylamine and N-methylmorpholine.

11. The process according to claim 4, wherein the non-polar precipitating solvent is selected from the group consisting of ethyl ether, petroleum ether and mixtures thereof.

* * * * *